(12) United States Patent
Jansen et al.

(10) Patent No.: US 7,529,574 B2
(45) Date of Patent: May 5, 2009

(54) METHOD OF CONSTRUCTING A BIOSENSOR

(75) Inventors: Lawrence B. Jansen, Portland, OR (US); W. Kenneth Ward, Portland, OR (US); Ellen Anderson, Tualatin, OR (US)

(73) Assignee: iSense Corporation, Wilsonville, OR (US)

( * ) Notice: Subject to any disclaimer, the term of this patent is extended or adjusted under 35 U.S.C. 154(b) by 128 days.

(21) Appl. No.: 10/640,980

(22) Filed: Aug. 14, 2003

(65) Prior Publication Data

US 2005/0038330 A1   Feb. 17, 2005

(51) Int. Cl.
*A61B 5/00* (2006.01)

(52) U.S. Cl. ............ 600/345; 600/347; 600/365

(58) Field of Classification Search ............ None
See application file for complete search history.

(56) References Cited

U.S. PATENT DOCUMENTS

| | | | | |
|---|---|---|---|---|
| 3,898,147 A | * | 8/1975 | Niedrach | 204/414 |
| 3,900,382 A | * | 8/1975 | Brown, Jr. | 204/403.06 |
| 3,957,613 A | * | 5/1976 | Macur | 204/412 |
| 4,354,913 A | * | 10/1982 | Pungor et al. | 204/403.08 |
| 4,388,166 A | * | 6/1983 | Suzuki et al. | 204/403.05 |
| 4,565,666 A | * | 1/1986 | Cahalan et al. | 264/267 |
| 4,671,288 A | * | 6/1987 | Gough | 600/347 |
| 4,703,756 A | * | 11/1987 | Gough et al. | 600/347 |
| 4,891,125 A | * | 1/1990 | Schultz | 204/435 |
| 4,919,141 A | * | 4/1990 | Zier et al. | 600/345 |
| 5,063,081 A | * | 11/1991 | Cozzette et al. | 435/4 |
| 5,165,407 A | * | 11/1992 | Wilson et al. | 600/345 |
| 6,144,871 A | * | 11/2000 | Saito et al. | 600/395 |
| 6,259,937 B1 | * | 7/2001 | Schulman et al. | 600/345 |
| 2002/0169369 A1 | * | 11/2002 | Ward et al. | 600/347 |

* cited by examiner

*Primary Examiner*—Robert L. Nasser, Jr.
(74) *Attorney, Agent, or Firm*—Schwabe, Williamson & Wyatt, P.C.

(57) ABSTRACT

A method of creating an analyte sensor. The method starts with the step of providing an electrochemically active surface. Then, at least one nub made of dielectric material and extending transversely outwardly from the electrochemically active surface is created. A curable liquid is applied to the electrochemically active surface and the nub and is then cured. In this process, the nub, which could be one of several nubs, serves to support the liquid before and during the curing.

19 Claims, 1 Drawing Sheet

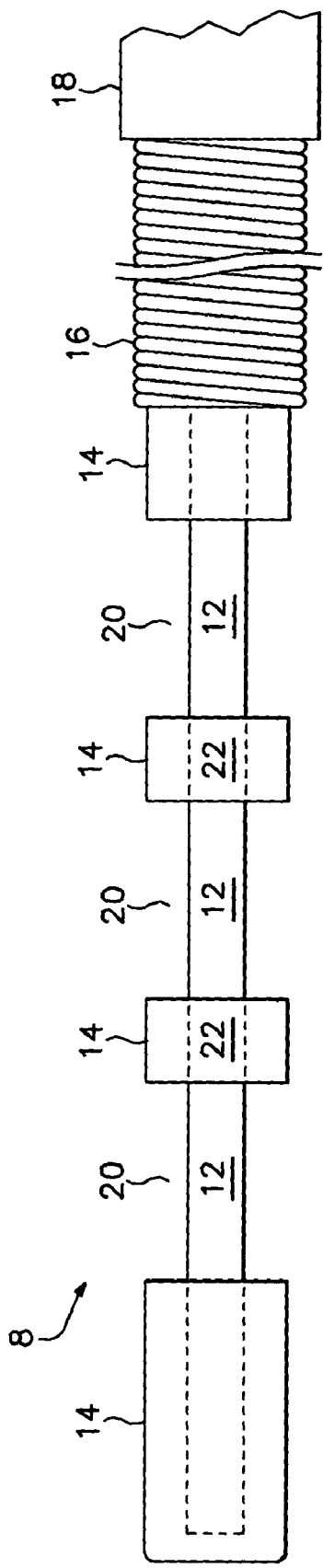
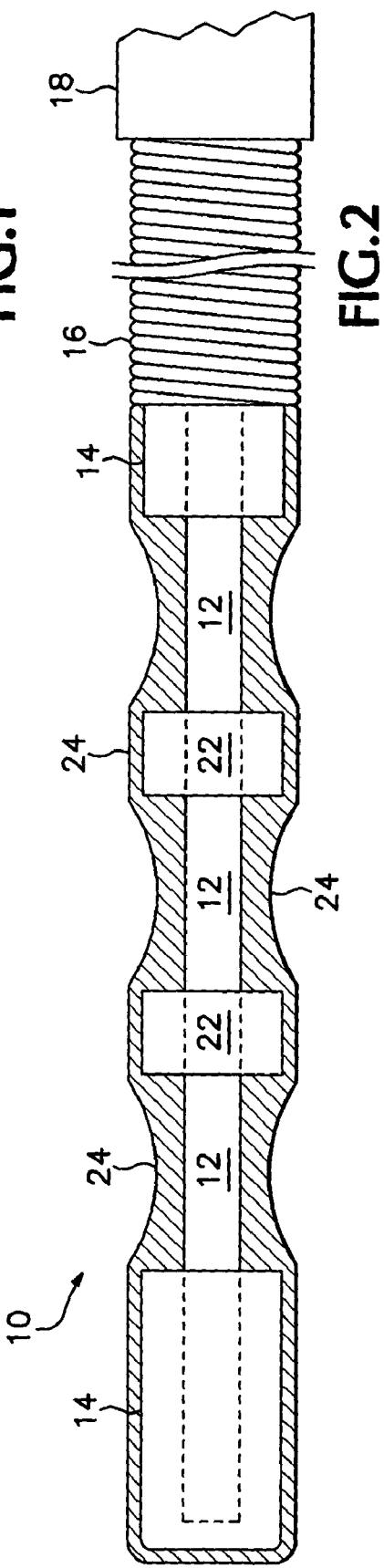

METHOD OF CONSTRUCTING A BIOSENSOR

BACKGROUND OF THE INVENTION

In the design and manufacture of an indwelling glucose sensor, a problem has been encountered in the application of viscous liquid layers of material, which are then cured, over the electrochemically active (platinum) surface. It is desirable to have an active surface area that is on the order of about a square millimeter. Unfortunately, when dip coating viscous liquids onto this relatively large area, it has been quite difficult to construct a coating having a thickness sufficient to produce an adequate response to the presence of glucose.

SUMMARY OF THE INVENTION

In a first separate aspect, the present invention is an indwelling analyte sensor that has an active sensing region. This sensing region includes an electrochemically active surface and a membrane system that adheres to the electrochemically active surface. In addition, at least one nub of dielectric material extends outwardly from the electrochemically active surface and serves as a supportive structure to the membrane system.

In a second separate aspect, the present invention is a method of creating an analyte sensor. The method starts with the step of providing an electrochemically active surface. Then, at least one nub made of dielectric material and extending transversely outwardly from the electrochemically active surface is created. A curable liquid is applied to the electrochemically active surface and is then cured. In this process, the nub, which could be one of several nubs, serves to support the liquid before and during the curing.

The foregoing and other objectives, features and advantages of the invention will be more readily understood upon consideration of the following detailed description of the preferred embodiment(s), taken in conjunction with the accompanying drawings.

BRIEF DESCRIPTION OF THE DRAWINGS

FIG. 1 is a side view of a work piece formed as part of the construction of a biosensor using the method of the present invention.

FIG. 2 is a side view of a sensor constructed from the work piece of FIG. 1.

DETAILED DESCRIPTION OF THE PREFERRED EMBODIMENT(S)

In a preferred embodiment of an analyte (typically glucose) sensor 10 (FIG. 2) a 178 micron thick platinum wire 12 is coated with a 25 micron thick polyimide layer 14. A silver wire 16 is wrapped about a portion of layer 14. In addition, a stainless steel retractor lead 18 forms a portion of sensor 10.

Three cavities 20, each 2 mm long, are formed by laser ablating polyimide layer 14 to form a work piece 8 (FIG. 1). The polyimide between the cavities 20, forms a set of annular plates 22, that are supported by the adherence of the polyimide 14 onto wire 12. In an embodiment, nubs, such as annular plates 22, may be spaced longitudinally from the active surface of wire 12. After the laser machining operation, the work piece is ready to be dip coated with the material 24 that permits it to detect glucose. Typically, material 24 is comprised of a set of layers that are constructed through a sequence of dip coating operations interspersed with curing operations. These layers typically include an interferent excluding layer, a glucose oxidase layer and a permselective layer as described in U.S. Pat. No. 5,165,407, which is hereby incorporated by reference as if fully set forth herein. The surface of each viscous fluid tends to form a shape somewhat like a catenary curve between plates 22. Accordingly a greater portion of viscous fluid adheres than would adhere without the presence of plates 22. This greater thickness, especially for glucose oxidase layer is very important in the creation of a robust response to the presence of glucose and oxygen.

The terms and expressions that have been employed in the foregoing specification are used as terms of description and not of limitation. There is no intention, in the use of such terms and expressions, of excluding equivalents of the features shown and described or portions thereof, it being recognized that the scope of the invention is defined and limited only by the claims which follow.

The invention claimed is:

1. An indwelling analyte sensor, comprising:
   an electrochemically active surface;
   at least two nubs of dielectric material extending outwardly from said electrochemically active surface and forming a cavity along said electrochemically active surface and between said at least two nubs; and
   a membrane system comprising an enzyme layer, said enzyme layer surrounding said at least two nubs and said electrochemically active surface at least along said cavity.

2. The sensor of claim 1, wherein at least one of said at least two nubs is in the form of a plate.

3. The sensor of claim 1, wherein at least one of said at least two nubs comprises an annular plate.

4. The sensor of claim 1, wherein said electrochemically active surface is defined as part of a lengthwise body.

5. The sensor of claim 4, wherein said lengthwise body is circular in cross-section.

6. The sensor of claim 1, wherein at least one of said at least two nubs is displaced longitudinally from said electrochemically active surface.

7. The sensor of claim 1, wherein said membrane system includes multiple membranes.

8. The sensor of claim 1, wherein said membrane system defines an external surface of said sensor.

9. An indwelling analyte sensor, comprising:
   an electrochemically active surface defining a sensing region along a portion of said electrochemically active surface;
   a plurality of nubs of dielectric material extending outwardly from said electrochemically active surface, said plurality of nubs spaced along said electrochemically active surface; and
   a membrane system comprising an enzyme layer, said enzyme layer surrounding said sensing region of said electrochemically active surface to form an active sensing region and surrounding said plurality of nubs.

10. The sensor of claim 9, wherein said electrochemically active surface extends through at least two of said plurality of nubs.

11. The sensor of claim 9, wherein said membrane system defines a substantially catenary curve-shaped surface between at least two of said plurality of nubs.

12. The sensor of claim 9, wherein said membrane system has an outer surface and said outer surface defines a concave curve curving toward said electrochemically active surface between at least two of said plurality of nubs.

13. The sensor of claim 9, wherein at least one of said at least two nubs is in the form of a plate.

14. The sensor of claim 9, wherein at least one of said at least two nubs comprises an annular plate.

15. The sensor of claim 9, wherein said electrochemically active surface is defined as part of a lengthwise body.

16. The sensor of claim 15, wherein said lengthwise body is circular in cross-section.

17. The sensor of claim 9, wherein at least one of said at least two nubs is displaced longitudinally from said electrochemically active surface.

18. The sensor of claim 9, wherein said membrane system includes multiple membranes.

19. The sensor of claim 9, wherein said membrane system defines an external surface of said sensor.

* * * * *